United States Patent [19]
Dietz

[11] Patent Number: 5,485,833
[45] Date of Patent: Jan. 23, 1996

[54] BREATH EXPOSURE SYNCHRONIZER

[76] Inventor: Henry G. Dietz, 80 Salisbury Ave., Garden City, N.Y. 11530

[21] Appl. No.: 258,568

[22] Filed: Jun. 10, 1994

[51] Int. Cl.$^6$ ................................................. A61M 16/00
[52] U.S. Cl. ................................ 128/204.23; 128/204.21; 128/205.23
[58] Field of Search ..................... 128/204.18, 204.21, 128/204.23, 716, 722, 205.23

[56] References Cited

U.S. PATENT DOCUMENTS

| | | | |
|---|---|---|---|
| 3,504,670 | 4/1970 | Hoel | 128/204.19 |
| 3,524,058 | 8/1970 | Robertson et al. | |
| 3,993,995 | 11/1976 | Kaplan et al. | |
| 4,289,142 | 9/1981 | Kearns | 128/716 |
| 4,387,722 | 6/1983 | Kearns | 128/716 |
| 4,519,387 | 5/1985 | Durkan et al. | 128/204.23 |
| 4,612,928 | 9/1986 | Tiep et al. | 128/204.23 |
| 4,686,975 | 8/1987 | Naimon et al. | 128/204.23 |
| 5,052,400 | 10/1991 | Dietz | 128/722 |
| 5,070,321 | 12/1991 | Einhorn et al. | 128/722 |
| 5,134,886 | 8/1992 | Ball | 128/204.23 |

*Primary Examiner*—Aaron J. Lewis

[57] ABSTRACT

Breath Exposure Synchronizer senses respiratory activity and indicates when it is the proper time to expose X-ray film to prevent blurring of radiographs due to voluntary motion of breathing. It indicates inhalation, when the breath is held, exhalation, and acts as a monitor to detect breathing in humans and animals.

When used with Magnetic Resonance Imaging, it has the advantage of having no electrical connections to the patient. Electrical currents can be induced in electrical connections by the radio frequency magnetic fields used during imaging that can be harmful.

Breathing is detected by a single use nasal cannula sensor.

1 Claim, 3 Drawing Sheets

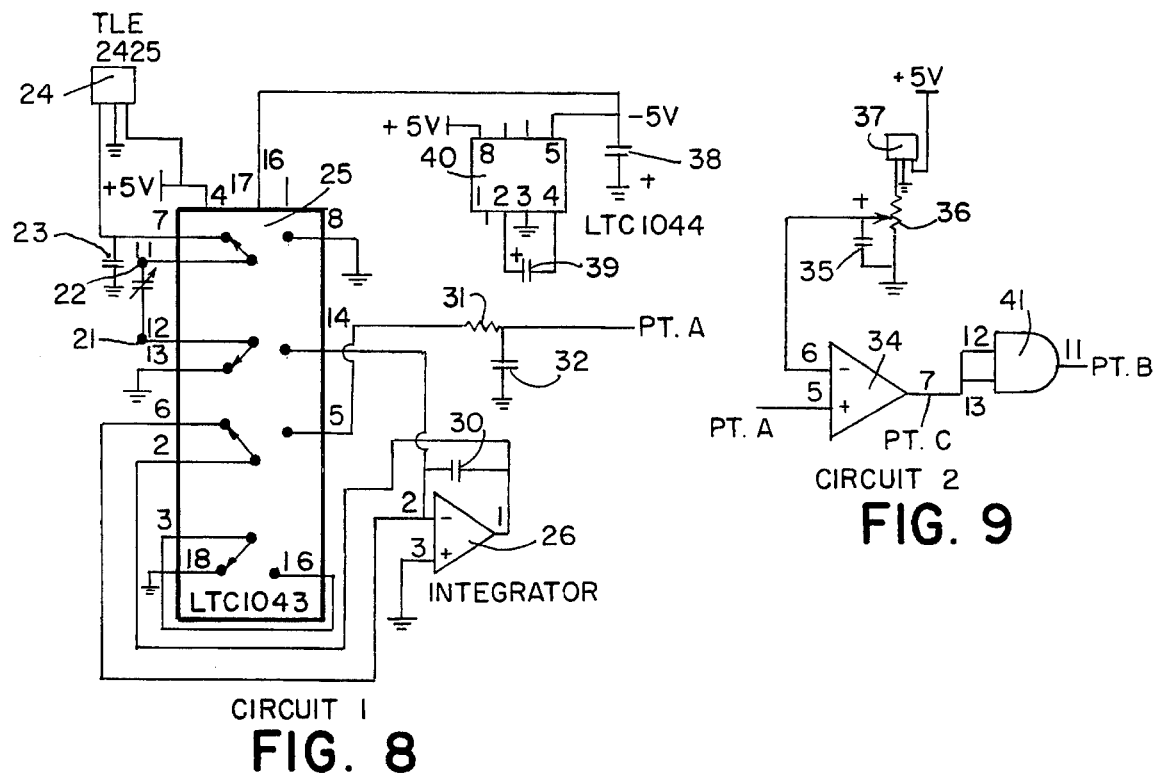
FIG. 8 CIRCUIT 1
FIG. 9 CIRCUIT 2
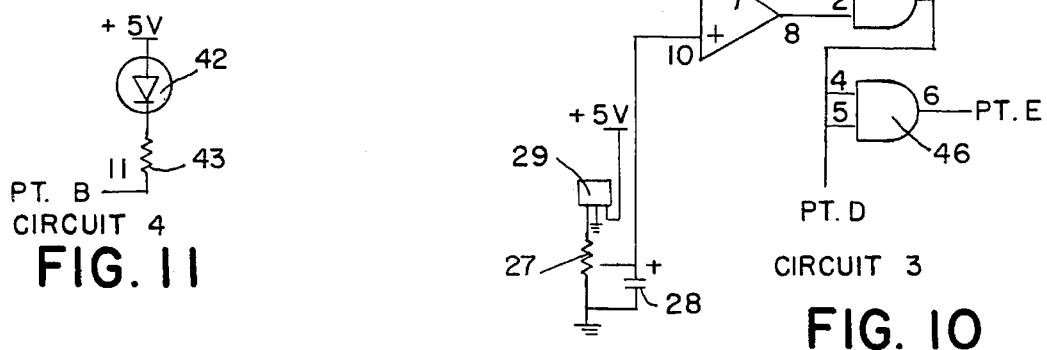
FIG. 10 CIRCUIT 3
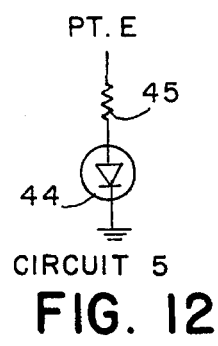
FIG. 11 CIRCUIT 4
FIG. 12 CIRCUIT 5
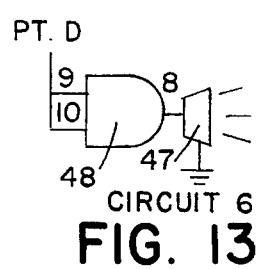
FIG. 13 CIRCUIT 6

BREATH EXPOSURE SYNCHRONIZER

BACKGROUND OF THE INVENTION

This invention relates to a monitor of breathing that can detect the low positive pressure of exhalation at the nostrils of an air breathing human or animal, in like manner the negative pressure of inhalation, and the lack of any pressure when breathing is suspended.

This invention is a simplified use of the method described in patent pending for "Monitor of Low Pressure Intervals with Control Capabilities" filed Aug. 13, 1993 by Henry G. Dietz (application Ser. No. 08/106,083). However, the invention in this application is used for a completely new use, and has a sensor with two functions instead of the single function sensor used in the pending application.

In patent pending (application Ser. No. 08/106,083), the sensor is used to detect the on-set of inhalation with control capabilities. This application uses a two function sensor, one function for detecting inhalation, and a second function for detecting exhalation, with detection of breath being suspended when the two functions detect no breathing.

The experience gained from the development of the patent pending resulted in an effort to develop a device that could use the sensor of the patent pending to create a new useful product of low cost that enables one to snychronize exposure of film to actual respiration of a patient. It makes it possible to display patient's breathing to ascertain that the radiographer's instructions are being followed by the patient. It is an excellent training aid that can show the importance of respiration as part of the X-ray procedure.

Breath Exposure Synchronizer allows studies on how a patient breathes. For example, it shows a second breath often can be better than the first as more air can be inhaled on the second breath without the unsteadiness obtained in the first breath. It can be used to teach patients correct breathing procedures prior to being subjected to radiation. Its use results in less radiation exposure by reducing the need for repeat radiographs. The use of a nasal cannula for sensing eliminates the need for electrical connections to the patient, and makes the Breath Exposure Synchronizer suitable for use with MRI (Magnetic Resonance Imaging.)

SUMMARY OF THE INVENTION

Breath Exposure Synchronizer is an invention that enables a radiographer to synchronize the exposure of film to the actual respiration of a patient. It makes it possible to display a patient's breathing to ascertain that the radiographer's instructions are being followed by the patient.

Breath Exposure Synchronizer can aid the radiographer by providing greater cost efficiency, improved productivity, while producing consistently high quality films. These goals can be obtained, with added benefit to the patient, by reducing the need of repeat radiographs.

As a teaching aid, it can show how voluntary motion of breathing can cause blurring of X-ray films. Stress due to fear of the results of a diagnostic radiographic examination may result in an inability to fully follow instructions, which will be indicated by the Breath Exposure Synchronizer.

Breath Exposure Synchronizer can be useful for such X-ray procedure as taking chest roentgenograms when the patient's lungs must be fully expanded and not in motion. The quality of the X-ray taken can be adversely affected by chest movement. Breath Exposure Synchronizer for this procedure indicates full inspiration by a Red Light, followed by steady Green Light that indicates film should be exposed. This procedure is also correct for X-rays of the Sternum and Anterior Ribs.

For X-ray procedures requiring suspended respiration only, such as X-ray of the Humerus, Shoulder, Acromioclavicular, Scapula (lateral position), Bilateral Hips, Pelvis, Sacroiliac Joints, Cervical Spine, Cranium Skull series, Facial Bones, Nasal Bones, Zygomatic Arch, Optic Foramina, Orbits, Mandible, Temporomandibula joints, Paranasal Sinuses, Mastoids, Petrous Pyramids, or Mammography, are indicated by a steady Green light for proper exposure of film.

For X-ray procedures requiring full exhalation followed by suspended respiration, such as X-rays of the Abdomen, Clavicle, Coccyx, Sacrum, Lumbar Spine, Scoliosis Series, Spinal Fusion Series, Thoracic Spine, Espohagram, Barium Enema, Gallbladder (oral cholecystogram), Intravenous (Excretory), Urography, Cystography, or Voiding Cystourethrography, are indicated by No Light followed by steady Green Light that indicates when film should be exposed.

Breath Exposure Synchronizer requires no electrical connection to the subject. Breathing is detected by a single use nasal cannula sensor that can detect the extremely low pressure at the nasal cavities when inhalation or exhalation takes place, and indicates when respiration is suspended.

A Red Light indicates when inspiration is taking place. When the full inspiration position is obtained and respiration suspended, the Red Light goes out (indicating full inspiration position has been obtained) and the Green "No Breath" Light illuminates to indicate exposure should be made.

For X-ray procedures requiring full expiration, no lights indicate when expiration is taking place. When full expiration is obtained and respiration is suspended, a "No Breath" Green Light indicates exposure should be made.

For X-ray procedure requiring breathing simply be suspended, a "No Breath" Green Light indicates when exposure should be made.

Breath Exposure Synchronizer is battery powered, portable, and has a low battery indicator when battery needs replacement.

When used with Magnetic Resonance Imaging, it's ability to operate with no electrical cables to the subject results in no electrical currents being induced by the radio frequency magnetic fields used during imaging.

When Breath Exposure Synchronizer is used with Magnetic Resonance Imaging, it can be located as far as possible from magnetic field generating equipment using for example, a 25 foot air hose extension.

Breath Exposure Synchronizer is an excellent tool for teaching "Square Breathing" which reduces the need of blowing into a paper bag when hyperventilation occurs. Square breathing should be practiced and learned before the need occurs. A patient should count to 4 for each inhalation, count to 4 for holding his breath, and count to 4 while exhaling. Hyperventilation should be recognized as a possible symptom of heart problems, and square breathing should only be practiced on the advise of a physician.

Breath Exposure Synchronizer can be used for teaching athletes proper breathing. The greatest physical damage can occur if an athlete is struck when his lungs are expanded during inhalation.

Another use is for teaching "conscious breathing" where people are taught how to breath in a deliberate fashion. This can also be useful in practicing a form of Buddhism know as Zen which teaches the importance of breathing with meditation.

Features and objects of the Breath Exposure Synchronizer will be understood from the claims and appended drawings, in which it is to be noted that reference characters refer to the same parts throughout the various views:

FIG. 8 is a sensor interfacing circuit that converts changes in capacitance of the transducer connected to terminals 21 and 22 to a voltage. Point A voltage increases if the sensor is exposed to exhalation (pressure) and decreases if exposed to vacuum (inhalation).

Point A of Circuit #1 is interfaced to Point A of Circuit #2 of FIG. 9. Circuit #2 of FIG. 9 is a control circuit that detects inhalation (decrease in voltage). The signal at point C changes from 5 V (logic 1) to 0 V (logic 0) when inhalation occurs. The signal at Point B is a duplicate of signal at Point C. Point B of FIG. 9 is interfaced to Point B of circuit #4 of FIG. 11.

Circuit #4 of FIG. 11 is a LED to indicate inhalation. Point C of FIG. 9 is interfaced to Circuit #3 of FIG. 10.

Circuit #3 of FIG. 10 is a control circuit to detect exhalation (increase in voltage).

Point E of FIG. 10 is interfaced to Point E of FIG. 12 of Circuit #5. The LED of Circuit #5 indicates no respiration.

Point D of FIG. 10 of Circuit #3 is interfaced to Point D of Circuit #6 of FIG. 13. Circuit #6 is used to sound an alarm if there is no inhalation or exhalation.

| Activity | Green LED | Red LED | Alarm |
| --- | --- | --- | --- |
| No inhalation or exhalation | ON | OFF | ON |
| Inhalation | OFF | ON | OFF |
| Exhalation | OFF | OFF | OFF. |

DESCRIPTION OF THE PREFERRED EMBODIMENTS

Figure 1:
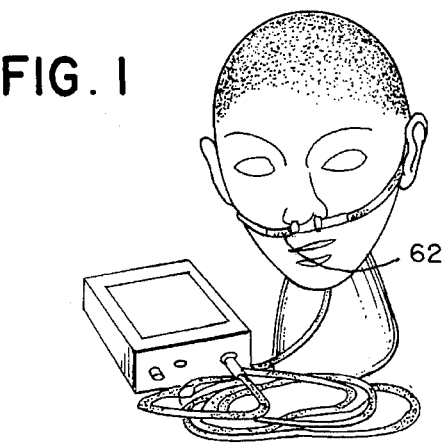
FIG. 1 is a diagrammatic view of Breath Exposure Synchronizer with nasal cannula.
Figure 2:
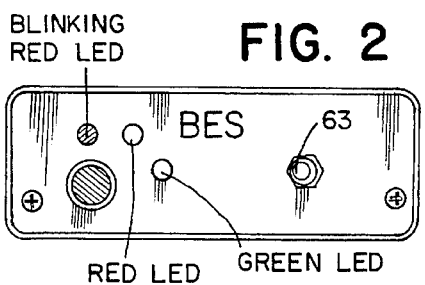
FIG. 2 is a diagrammatic front view of the Breath Exposure Synchronizer.
Figure 3:
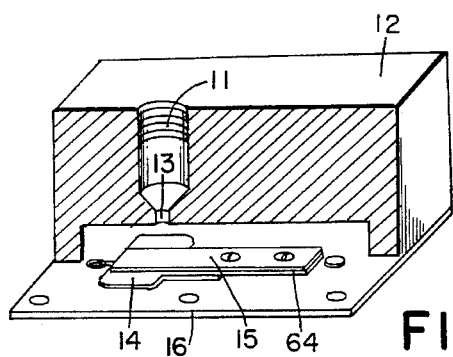
FIG. 3 is a cutaway isometric drawing of the sensor.

A patient is connected to a nasal cannula 62, FIG. 1 or a similar device, and the other end of the cannula is attached to an outlet connection 63, FIG. 2. The nasal cannula is used for the purpose of sensing respiration by detecting the negative pressure at the nostrils of the air breathing patient, the positive pressure of exhalation, and no pressure when there is no breath. The outlet connection 63, FIG. 2 is connected to female pipe thread 11, FIG. 3 of the sensor. FIG. 3 is shown cutaway through its center located in aluminum block 12. Negative pressure is received from subject's cannula 62 at the small hole opening 13, FIG. 3. This negative pressure causes a thin mica (or similar material) vane 14, FIG. 3, to be sucked up and hit the metal stop 15, FIG. 3.

Figure 4:
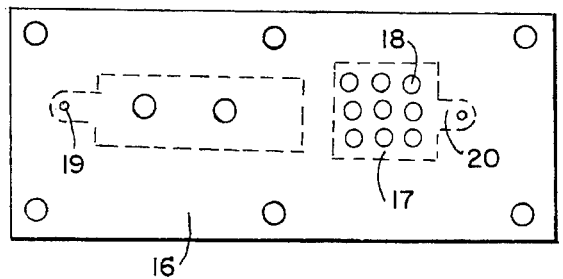
FIG. 4 is a bottom view of the sensor.

Vane 14 has a conductive coating on one side facing upward, with its insulated side adjacent to copper foil 17, FIG. 4 outlined with a dotted line on a printed circuit board 16, FIG. 4, facing upward. FIG. 4 shows printed circuit board 16 with its bottom facing up. The two plate capacitor is formed by vane 14 and copper foil 17 with the dielectric being mica (or similar material) approximately 0.001" thick. Vane 14 is sucked upward because there are 9 holes, 18 FIG. 4, under vane 14 to allow atmospheric pressure to force vane 14 upward when there is a negative pressure at hole 13. Vane 14 of FIG. 3 is sensitive to positive pressure being applied to small hole 13. This positive pressure is generated when patient exhales. When pressure is applied to vane 14, the vane is forced closer to copper foil 17 of FIG. 4.

Electrical connection to solder connection 19, FIG. 4, is made by clamping stop 15 and spacer 64 with two screws that screw into threaded holes in printed circuit board 16. Electrical connection 20, FIG. 4 is made by a wire soldered to copper foil 17. These two electrical connections make vane 14 a variable capacitor whose operation is dependent upon the inhalation and exhalation of patient wearing nasal cannula 62, FIG. 1. The value of capacitor is inversely proportional to the distance between the two plates and has a value in the picofarad range. Voltage applied to this capacitor is kept constant. The change in charge is determined by the position of vane 14 relative to copper foil 17.

Figure 5:
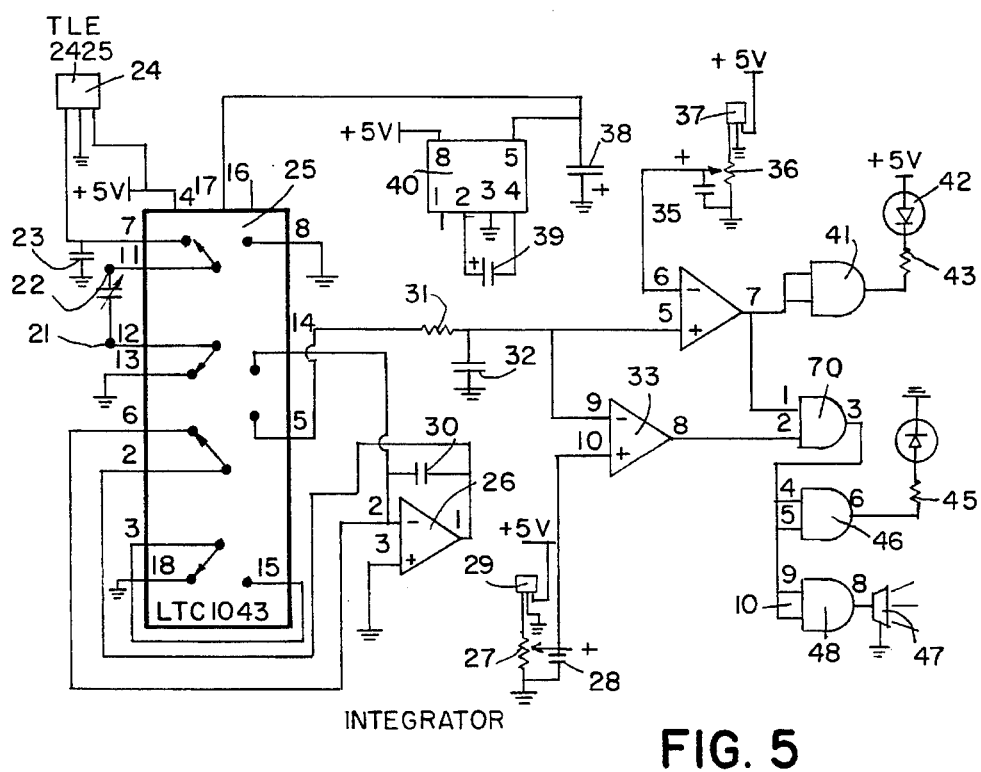
FIG. 5 is a schematic diagram of circuit used with the sensor.

FIG. 5 is a circuit diagram used with an inhalation and exhalation sensor, FIGS. 3 and 4. The sensor is connected to the circuit by electrical connections 21 and 22. Integrated chip 25 is a monolithic, charge-balanced, dual switched capacitor instrumentation building block which continuously charges and discharges the sensor connected to connections 21 and 22.

Chip 25 generates an internal two non-over lapping clock, phase 1 and 2. During phase 1 internal switches are connected in such a manner that the sensor's capacitance is charged to Q-CV and during this phase, the integrating capacitor 30 of the integrating system is shorted for the purpose of discharging. During phase 2, charge accumulated on the sensor's capacitance is dumped on capacitor 30. Output of integrator 26 is connected to chip 25 pin 2. Pin 2 alternates between pin 6 and pin 5 of IC chip 25. Pin 5 of chip 25, is filtered through an RC low pass filter using resistor 31 and capacitor 32 as shown in FIG. 5. The Breath Exposure Synchronizer requires a negative, as well as a positive, power supply which is provided by switch capacitor voltage converter 40 of FIG. 5, and capacitors 38 and 39 are used to stabilize 40. Capacitors 23 and 28 are used to bypass high frequencies to the ground.

Virtual ground chip 24 generates a 2.5 V reference voltage used by pin 7 of chip 25. Virtual ground chips 29 and 37 are also used to generate a stable 2.5 V reference for potentiometers 27 and 36. Resistors 43 and 45 are current limiting resistors to LEDs 42 and 44 which will illuminate respectively every time an inhalation or exhalation occurs. During no breath comparators 33 and 34 remain at logic 1. The output of comparator 34 is fed to input of buffer 41. When comparator 34 is at logic 1, LED 42 is turned off. The output of comparators 33 and 34 are fed to AND gate 70. The AND gate 70 generates a logic 1 if both of its inputs are logic 1, otherwise an output of logic 0 occurs. Output of gate 70 is fed to buffer gate 46 and 48. Both comparators 33 and 34 are at logic 1, therefore LED 44 and buzzer 47 are enabled.

During inhalation comparator 34 changes from logic 1 to logic 0, thus enabling LED 42, but disabling LED 44 and buzzer 47. During exhalation comparator 34 does not change but comparator 33 changes from logic 1 to logic 0. Comparator 34 is at logic 1, thus LED 42 is disabled and gate 70 outputs logic 0. At this time, LED 44 and buzzer 47 or green LED are also disabled.

Figure 6:
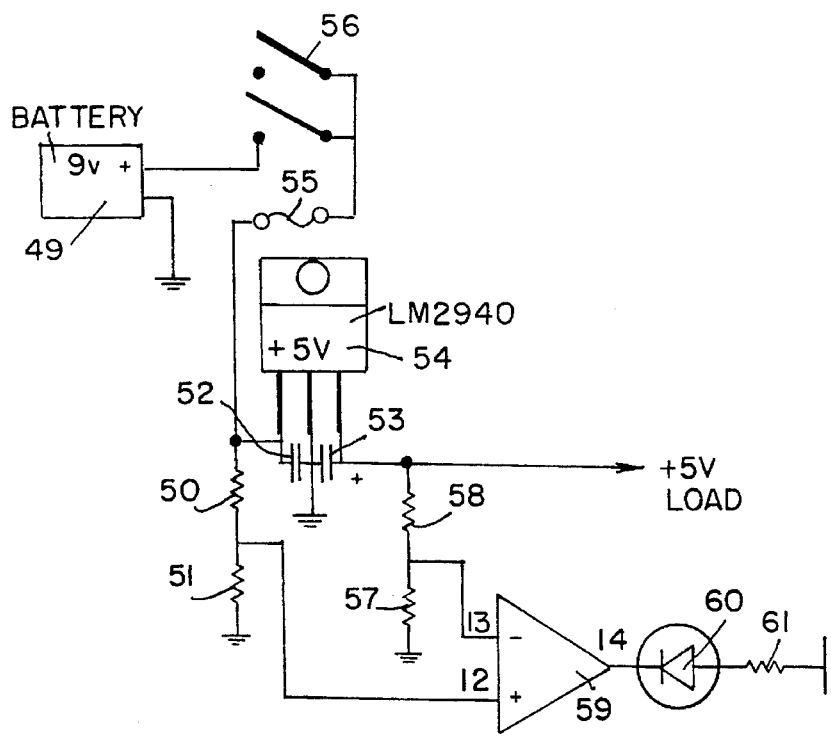
FIG. 6 is a schematic diagram of power supply and low battery indicator.
Figure 7:
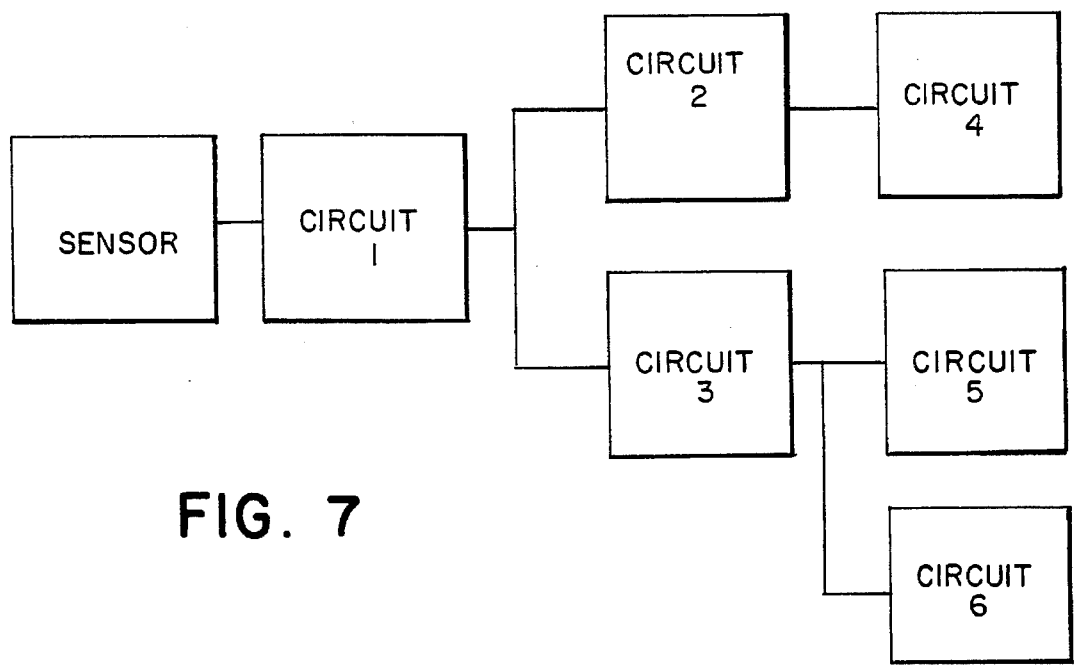
FIG. 7 is a block diagram of Breath Exposure Synchronizer.

FIG. 6 is a circuit diagram of power supply and low battery indicator used in the Breath Exposure Synchronizer. The Breath Exposure Synchronizer operates from a 9 volt battery 49, FIG. 6.

Power switch 56 controls the on/off function of the Breath Exposure Synchronizer. Fuse 55 protects circuits from high current from battery 49, FIG. 6, in case of a short.

Voltage regulator 54 is used for regulating the 9 volts to a constant plus 5 volt source. Capacitors 52 and 53 are used to prevent voltage regulator 54 from oscillating, and filtering of input supply respectively. The Breath Exposure Synchronizer requires a low battery detection system, which is incorporated by using comparators 59 along with resistors 50, 51, 57, 58, and LED 60 as shown in FIG. 6. Red LED 60 flashes whenever battery 49 voltage goes below the set volts. Resistor 61 is a current limiting resistor for LED 60.

While the invention has been particularly shown and described with references to the preferred embodiments thereof, it will be understood by those skilled in the art that various alterations in form and detail may be made therein without departing from the spirit and scope of the invention.

I claim:

1. A breath exposure synchronizer for sensing flow during inhalation, exhalation and lack of any breath flow in order to aid a radiographer in properly synchronizing exposure of X-ray film to avoid blurring of radiographs due to voluntary body movement, comprising:

means including a capacitance sensor for sensing a patient's breath flow during inhalation, exhalation and a lack of breath flow;

means including a nasal cannula for applying a patient's breath flow to said capacitance sensor;

said capacitance sensor including a movable pressure responsive vane having opposite sides and a conductive coating on at least one of the sides, the vane being fastened on one side only;

said vane moving in one direction responsive to negative pressure of breath flow being applied thereto during patient inhalation, and moving in another direction responsive to positive pressure of breath flow being applied thereto during exhalation;

said capacitance sensor further including means responsive to sensed patient inhalation and sensed patient exhalation for generating a first visual signal; and means responsive to no breath flow for generating a second visual signal, said visual signals being provided to enable a radiographer to properly synchronize exposure of X-ray film with a patient's respiratory cycles to avoid blurring of radiographs.

* * * * *